United States Patent [19]
Livingston-Wheeler et al.

[11] Patent Number: 4,643,970
[45] Date of Patent: Feb. 17, 1987

[54] PRODUCTION OF HCG

[76] Inventors: Virginia Livingston-Wheeler, The Livingston Medical Center, 3232 Duke St., San Diego, Calif. 92110; John J. Majnarich, Seattle, Wash.

[21] Appl. No.: 469,004

[22] Filed: Feb. 23, 1983

Related U.S. Application Data

[63] Continuation of Ser. No. 171,280, Jul. 23, 1980, abandoned, which is a continuation of Ser. No. 27,516, Apr. 5, 1979, abandoned, which is a continuation-in-part of Ser. No. 957,206, Nov. 3, 1978, abandoned, Ser. No. 878,483, Feb. 16, 1978, abandoned, Ser. No. 686,896, May 17, 1976, abandoned, Ser. No. 672,965, Apr. 2, 1976, abandoned, and Ser. No. 295,720, Oct. 6, 1972, abandoned.

[51] Int. Cl.$^4$ .......................... C12P 21/00; C12R 1/45
[52] U.S. Cl. ........................................ 435/68; 435/884
[58] Field of Search ............................................ 435/68

[56] References Cited

U.S. PATENT DOCUMENTS 4,410,510 10/1983 Wheeler et al. ..................... 424/92

Primary Examiner—Lionel M. Shapiro

[57] ABSTRACT

Method for the production of chorionic gonadotropin (CG) with properties similar to those of human CG (HCG) from a microorganism or mutant thereof isolated by natural or hybridization procedure from the body or body extract carrier of a malignant tumor carrier and having the capacity to synthesize the polypeptide hormone known as human chorionic gonadotropin in its total form or in its sub-units ($\alpha$ & $\beta$) which comprises:

(a) culturing the microorganism or mutant thereof in a culture media;

(b) incubating the culture of the microorganism or mutant thereof, whereby the microorganism or mutant thereof in vivo produces a crude material containing chorionic gonadotropin and/or its sub-units ($\alpha$ & $\beta$);

(c) separating the crude material containing chorionic gonadotropin and/or its sub-units ($\alpha$ & $\beta$) from the culture media and the microorganism or mutant thereof.

9 Claims, No Drawings

PRODUCTION OF HCG

This application is a continuation of U.S. patent application Ser. No. 171,280, filed July 23, 1980, (now abandoned) which is a continuation of application Ser. No. 027,516, filed Apr. 5, 1979 (now abandoned), which is a continuation-in-part of the following applications:
  (i) application Ser. No. 957,206, filed on Nov. 3, 1978;
  (ii) application Ser. No. 878,483, filed on Feb. 16, 1978 (now abandoned);
  (iii) application Ser. No. 686,896, filed on May 17, 1976 now abandoned;
  (iv) application Ser. No. 672,965, filed on Apr. 2, 1976 (now abandoned);
  (v) application Ser. No. 295,720, filed on Oct. 6, 1972, now abandoned.

Evidence for the etiological relationship of Progenitor cryptocides to neoplastic disease has been documented over a period of years. Its cultural properties, staining characteristics, and morphology have been fully described. Its filterable bodies have been measured by electron microscope and found similar in size to some viruses. The pathology produced in experimental animals has been reported. It has also been demonstrated in fresh blood samples examined by darkfield and phase microscopy. More recently, immunological studies in guinea pigs have shown cross-reactivity with *M. tuberculosis*. In addition, the production by P. cryptocides in vitro of a parahormone or analogue of human chorionic gonadotropin is described. Its identification by bioimmunological and radioimmunoassay methods has been established. A culture of Progenitor cryptocides was deposited in the American Type Culture Collection, Accession No. 31874.

PREPARATION AND DEMONSTRATION OF CHORIONIC GONADOTROPIN PRODUCED BY PROGENITOR CRYPTOCIDES IN VITRO

BACTERIAL METHODOLOGY

1. Culture media Bath Production

The culture media has been fluid thioglycollate medium without indicator. The dry mixed medium is purchased in 1 lb. bottles and prepared as directed so that each liter furnishes the following:

TABLE I

|  | Grams per liter |
|---|---|
| Trypticase | 17.0 |
| Phytone | 3.0 |
| Dextrose | 6.0 |
| Sodium chloride | 2.5 |
| Sodium thioglycolate | 0.5 |
| Agar | 0.7 |
| l-cystine | 0.25 |
| sodium sulfite | 0.1 |

Improved results up to ten-fold yield are obtained by the addition of galactose in amounts equal to or less than the amount of dextrose and optimum results are obtained by using the same amount of galactose in place of dextrose.

30 grams of the dehydrated material is suspended in a liter of distilled water and heated on a Corning hot plate agitated by a magnetic stirring bar. Heating is continued for about 2 minutes after boiling. The medium is then sterilized in an autoclave at 120° C., 15 lbs. pressure for 15 minutes.

II. CG Organism - Innoculation

The organism used for innoculation of the sterile broth is a single colony from blood agar plates (phenylethyl alcohol). The organism is from patient urine isolates or blood cultures which exhibit acid-fastness. It is Seitz filterable, found in the human blood stream. Incubation is carried out on an Incushaker at 37° C. The flasks are gently rocked. The incubation time has varied from 5 to 21 days. In all cases the growth produced good turbidity in 3 to 4 days. The time of maximum CGH production is considered as about 5-7 days. However little CGH is detected before the fifth day of incubation.

III. Isolation of CG

The entire culture media comprising organisms and broth is acidified to pH 4.5-5.0 by the addition of glacial acetic acid (75-100 ml. per 10 liters). Next 4 volumes or 40 liters of C.P. acetone are added to the 10 liter mixture producing a white precipitate.

The mixture is allowed to sit overnight at room temperature and the precipitate is recovered either by filtration or centrifugation. The final precipitate is washed with 10 ml. of dry acetone and then allowed to air dry after decanting the acetone supernatant.

Further purification of the CG hormone-like (CGH-like) material can be done by resuspending the sample in distilled water. The CGH-like material is water soluble whereas the proteins and associated lipids are water insoluble. Centrifugation and/or filtration at this stage will remove the oily substances and reddish plates to yield grey-white crystals. The CGH-like material can be reprecipitated from the water phase with 4 volumes of acetone.

This air dried fraction is always colored (tan or reddish brown). 10 mg. of this crude material dissolved in 10 ml. of distilled water is then used in the Pregnosticon test system, (Ortho). In the actual test only 0.1 ml. is used. The reaction is almost always a plus 4 reading.

CHORIONIC GONADOTROPIN DETERMINATIONS IN CONTROL ORGANISMS

Table I

The following score system was used:

| No reaction: | less than 750 I.U./liter | 0 | 0 |
|---|---|---|---|
|  | 750-7,5000 I.U./liter |  | 1 |
|  | 7,500-75,000 I.U./liter |  | 2 |
|  | 75,000-375,000 I.U./liter |  | 3 |
|  | Over 375,000 I.U./liter |  | 4 |

The results are presented in the following table.

TABLE II

| NAME | VISUAL SCORE | BIOASSAY |
|---|---|---|
| *Staphylococcus aureaus* | neg. | neg. |
| *Pseudomonas aruginosa* | neg. | neg. |
| *Salmonella typhosa* | neg. | neg |
| *Bacillus subtilis* | neg. | neg. |
| *Klebsellia pneumonia* | neg. | neg. |

CONTINUOUS BATCH PRODUCTION

IV. Bacterial Strains

The Progenitor crytocides used was an isolate from a cancer patient which produced Chorionic gonadatropin-like material. The organism is a gram positive coccin which on transfers from various media showed intermittent acid-fastness.

V. Medium

The liquid media consisted of 17 grams of Trypticase soy (Baltimore Biological Laboratory, Cockeysville, Md.), 10 grams yeast extract (BBL), 5 grams galactose and 2.5 grams of $K_2HPO_4$ per liter. The final PH was 7.2.

Cultures were maintained on Mueller-Hinton slants. Overnight growth of bacteria was the usual innoculum source. Slants of the organisms were kept in the refrigerator at 5° C. for future reference.

Shake flasks containing 250 ml. media in 500 ml. Erlenmeyer flasks were innoculated with a single colony from a culture from the Mueller-Hinton slant.

VI. Fermentation Conditions

A 20 liter lot of Trypticase-yeast extract medium was used in a 28 liter fermentor (New Brunswick Scientific Company, Edison, N.J.). The temperature was maintained at 37° C. Agitation was set at 400 RPM. Sparging was maintained at a rate of 10 liter of air per minute.

The media was sterilized at 15 pounds pressure, 250° F. for 45 minutes. The medium was cooled and innoculated with an overnight (12 hours) 250 ml. shake flask of the organism. After a fermentation of 20 hours, new media was introduced continuously at the rate of six liters per hour.

The new sterile media was supplemented with 3.5% dextrose and 3.5% galactose. The fermentor was equipped with pH control so that sterile 5N sodium hydroxide could be added on demand basis to maintain the pH at 7.2.

The harvest pump was set to pump at six liters per hour, thus the addition of new media and harvest rate were set at the log phase of the organism. The harvested culture was then centrifuged (18,000 RPM) with a continuous flow Cepa centrifuge Model Z41. The cells were collected as a paste, which was 25% solids, yield was 40 g./liter.

Determination of chorionic gonadotropin was performed on acetone precipitate of 100 ml. aliquots of a fermentation product. The test was carried out using the immuno-diagnostic pregnancy test (Pregnosticon ®) manufactured by Organon. The range of international units was determined by dilution of precipitate.

The bacterial or cryptocides produced represents 1 billion organisms/cc. To each 25 ml. suspension, without further treatment, was added 100 ml. acetone. The filtrate was discarded. CG determinations were carried out on the water soluble portion of the precipitated material.

In vitro studies conducted in a 2 liter flask containing the cryptocides produced CG which exhibited grown microbes at a 4 plus level measurable at the end of 10 days in terms of 750,000, units of CGH.

FINAL PURIFICATION OF CG

Chorionic gonadotropic hormone (CGH) was isolated from acetone precipitates of 120 hours growths of Progenitor cryptocides. All of the chorionic gonadotropin hormone preparations prepared by the acetone precipitation of cultures of Progenitor cryptocides were variable color and are pyrogenic when injected into rabbits.

The preparation containing 0.9 to 1.6 I.U./mg. chorionic gonadotropin. When redissolved in distilled water, these solutions gave a yellow to brown color. They were purified by percolation through a basic cellulose resin column which produced a white product without the pyrogenic effect.

Ten grams of a crude C.G., prepared from a 120 hour culture of Progenitor cryptocides and prepared as an acetone powder having an activity of approximately 100,000 units per gram as determined by Wampole Laboratories test kit, was dissolved in 200 cc acetate buffer at pH 6.0 (0.1 M sodium acetate. Twenty grams of DEAE-cellulose was washed with 500 ml. of acetate buffer until it yielded a pH 6.0 filtrate. The cellulose was then packed on a 20 mm by 100 mm column. The hormonal solution was then introduced and allowed to percolate through the column at a speed of 2–4 ml/minute. A colored band was formed near the top of the column while the percolate was colorless. After percolation, the column was washed twice with an additional 50 ml. of 0.1 M sodium acetate buffer solution and added to the total percolate. The total volume was measured (700 ml) to which was added five volumes of acetone (3500 ml) and placed in the ice box overnight. The precipitate that resulted was collected by centrifugation in one liter cups at 3000 RPM in a refrigerated centrifuge. The precipitate was washed once with cold acetone and then dried in a vacuum overnight. The yield was 1.10 gram with 80,000 units activity per gram, approximately an 80% recovery in activity and 90% weight reduction.

Pyrogen testing was done using three rabbits for the original material injecting ten units activity dissolved in 10 ml. sterile saline. The average temperature rise was 2.1° per rabbit. The purified material was injected at 100 units activity per ml. into each of three rabbits, and the average temperature rise was 0.2° C. per rabbit. Thus, using a basic cellulose column to purify CG results in a purer preparation suitable for medical use.

Agglutinates with rabbit CGH-antiserum evidences the CGH produced in accordance with the present invention equivalent or identical to human CG (HCG). Agglutination is performed by mixing one drop of rabbit antiserum (supplied by Cal Bio Chem) with one drop of a water solution of HCG which gives an immediate precipitant reaction to the slide, which is a measure of specificity of the CGH.

RADIMIMMUNOASSAY TECHNIQUE FOR ISOLATION OF CG DERIVED FROM PROGENITOR CRYPTOCIDES

Lyophylized bacterial preparation was reconstituted with 5 ml. distilled water. 100 µl of this preparation together with a tracer of I Human Chorionic Gonadotropin (100,000 counts/min.) was applied to the surface of a 1×15 cm column of polyacrylomide molecular exclusion gel "Biogel P-4". The column was eluted with 0.02 M phosphate buffer, pH 7.35, and collected in 0.5 ml. fractions. The bulk of the radioactivity was recovered in tubes 6, 7, 8, 9 and 10 (3–5 ml.). These fractions were combined, and this was assayed for CGH by radioimmunoassay, sensitive to 0.25 MIU. Two other later fractions (No. 24 and No. 63) were assayed at the same time. The combined early fraction was found to contain a large amount of HCG, with a potency exceeding 10 IU per 10 µl or reconstituted preparation. The other two fractions contained no HCG. Thus, the fact that the material emerged from the gel column at precisely the same fraction as authentic I HGC, coupled with its specific immuno-reactivity toward anti-HCG in the radioimmunoassay, strongly suggests its close identity with chorionic gonadotropin, with respect to both its molecular weight and size, and its immunological properties.

The following hormones were checked and found absent in the bacterial extract: Cortisol, testosterone, thyroid stimulating hormone (TSH), growth hormone (GH) and follicle stimulating hormone (FSH).

The antiserum made against the whole extract of cryptocides and that made against the purified fractions (CG) from cryptocides were both positive when checked with HCG, that is, they both found HCG in an antibody - antigen reaction.

It has been demonstrated that trypsin-like protease present in many tissues mimics HCG in the radioimmunoassay (RIA) and radioreceptor assay (RRA). Samples of an acetone powder of a culture of microorganism (Progenitor crypTocides?) was reconstituted in 0.01 M Tris-HCl, pH 7.4, and centrifuged. The crude bacterial extract demonstrated parallel dose-response curves to HCG (CR-119) in RIA using an antiserum (H93) generated against HCGB-COOH-terminal peptide and with RRA using bovine corpus luteum membranes. Addition of protease-inhibitors to the assay systems did not prevent the displacement of $^{125}$I-HCG in RIA and RRA. The equivalent hCG content of the acetone powder was 18 ng and 30 ng per mg as determined by RIA and RRA, respectively. The bacterial extract was chromatographed on Sephadex G-100. The CG factor determined by RIA and RRA was eluted at the position corresponding to that of $^{125}$I-hCG. Fractions containing small immunoreactive fragments reacting with anti-HCGB-COOH-terminal peptide were eluted, corresponding to a mol wt of about 11,000 daltons; whereas free α-subunit was not detected.

The CG factor was further purified by chromatography on Concanavalin A-Sepharose and on DEAE-Sephadex A-50. The CG factor did adsorb to Con A-Sepharose, suggesting that it possessed sugar moieties. On DEAE-Sephadex, it was eluted at a conductivity of 4.0–6.1 mmho. When the purified CG factor was subjected to sodium dodecyl sulfate gel electrophores it dissociated into two subunits. The mobilities of the subunits of bacterial CG were similar to those of authentic HCG subunits. The preparations of bacterial CG possessed significant biological activity in the rat uterine weight assay using three different doses. The biological potency of fractions obtained from each step of purification, namely, Sephadex G-100, Con A-Sepharose and DEAE-Sephadex A-50 were equivalent to 116,220 and 380 IU/mg, respectively. Thus, the properties of the bacterial CG factor and native hCG are similar, except for a difference in biological potency.

DIAGNOSIS OF CANCER AND PREGNANCY

It has been demonstrated that a filter passing pleomorphic microbe, P. cryptocides appears to be etiologically involved in the production of neoplastic disease in man and animals. It has been classified as belonging to the Actinomycetales and is intermittently acid-fast. Its pathology for experimental animals has been demonstrated. It is a blood parasite in both man and animal. It can be cultured readily on appropriate media from tumors and body fluids. Recently it has been shown that it cross-reacts with a number of mycobacters such as BCG, and Mycoplasma hominis when tested in the guinea pig. Toxic fractions from the cultures are known to increase the incidence of tumors in controlled mouse experiments. These fractions contain not only toxic antibiotic materials not characterized as yet but also crystalline material which appears to be CGH as such or as an analog or anahormone as demonstrated in experimental animal studies and by radioimmunoassay. The production of CG by P. cryptocides in vitro may explain the occurrence of the paraendocrine syndromes found in neoplasia.

SIGNIFICANCE OF THE EXPERIMENTAL EVIDENCE THAT CHORIONIC GONADOTROPIN IS PRODUCED BY PROGENITOR CRYPTOCIDES IN VITRO

Recently evidence that human chorionic gonadotropin antiserum appears to slow down experimental tumors in mice has been presented by Y. N. Sinha, Scripps Institution in La Jolla. Breaking the chain of host dominance by the bacterial CGH may prove to have therapeutic value. The bacterial counterfeit polypeptide CG appears to subvert from normal physiological pathways many complicated endocrine processes of the human host by action upon the pluripotential immature cell causing it to revert to its atavistic or primitive reproductive state since CG is concerned with rapid growth of embryonic or immature tissues before differentiation and maturation occur. CGH and subsequently bacterial CGH acts as a dominant hormone having the power to direct and alter many endocrine processes either by primary synthesis or related polypeptides or by secondary stimulation of steroidgenesis. Early in the neoplastic disease, destruction of tumor cells may benefit the host as might the reduction in numbers of the invading microbial parasite but late in the disease, endocrine and metabolic processes may be irreversibly damaged by the parasitic CGH so that removal of the tumor cells and destruction of the microbes may not restore normal endocrine balance since damage to the vital hormonal, immunological, enzymatic and metabolic processes may be irreversible and irreparable. Hope for the future may lie in universal vaccination or, barring that, early recognition of impending hormonal and immunological imbalance.

What is claimed is:

1. Method for the production of chorionic gonadotropin (CG), from the microorganism Progenitor cryptocides ATCC No. 31874 isolated by natural or hybridization procedure from the body or body extract carrier of a tumor having the capacity to synthesize the polypeptide hormone known as chorionic gonadotropin in its total form or in its subunits (α & β), which comprises:
   (a) culturing said Progenitor cryptocides in a culture media which contains galactose
   (b) incubating said culture of said Progenitor cryptocides, whereby said Progenitor cryptocides in vivo produces a crude material containing chorionic gonadotropin and/or its subunits (α & β); and
   (c) separating said crude material contgaining chorionic gonadotropin and/or its subunits (α & β), from said culture media and said Progenitor cryptocides.

2. The process as claimed in claim 1 wherein said Progenitor cryptocides is obtained from urine or blood cultures which exhibit acid-fastness and are cultured on blood agar plates of warm-blooded animals known to have cancer.

3. The process as claimed in claim 1 wherein said incubation was conducted for a period of 5 to 21 days.

4. The process as claimed in claim 1 wherein said subunit is separated from chorionic gonadotropin.

5. The process as claimed in claim 4 wherein said separation step (c) involves (i) acidifying the mixture of said culture media and crude material to a pH of 4.5 to 5, (ii) diluting said acidified mixture with water to form a precipitate containing chorionic gonadotropin, (iii) separating the chorionic gonadotropin-containing precipitate from mixture (ii), (iv) purifying the chorionic gonadotropin-containing precipitate, (v) suspending the precipitated chorionic gonadotropin-containing material in water to form a solution from the water-soluble fraction thereof, and (vi) centrifuging or filtering said water-soluble fraction to form the desired subunit $\beta$ crystals resulting therefrom.

6. The process as claimed in claim 5 wherein said aqueous solution of chorionic gonadotropin is hydrolyzed to form $\beta$ subunit-containing material and separating the resultant $\beta$ subunit therefrom.

7. The process as claimed in claim 1 wherein, in said culture media, an amount of galactose equal to the amount of said dextrose is added.

8. The process as claimed in claim 1 wherein said culture media is a fluid thioglycollate medium without indicator.

9. The process as claimed in claim 1 wherein, in said culture media, an amount of galactose equal to the amount of said dextrose is added.

* * * * *